(12) United States Patent
Barthold et al.

(10) Patent No.: US 11,376,133 B2
(45) Date of Patent: Jul. 5, 2022

(54) INTERVERTEBRAL IMPLANT

(71) Applicant: JOIMAX GMBH, Karlsruhe (DE)

(72) Inventors: Clemens Barthold, Karlsruhe (DE); Wolfgang Ries, Linkenheim (DE); Alexander Dürr, Markgröningen (DE)

(73) Assignee: JOIMAX GMBH, Karlsruhe (DE)

( * ) Notice: Subject to any disclaimer, the term of this patent is extended or adjusted under 35 U.S.C. 154(b) by 112 days.

(21) Appl. No.: 16/646,793

(22) PCT Filed: Sep. 5, 2018

(86) PCT No.: PCT/EP2018/000426
§ 371 (c)(1),
(2) Date: Mar. 12, 2020

(87) PCT Pub. No.: WO2019/052681
PCT Pub. Date: Mar. 21, 2019

(65) Prior Publication Data
US 2020/0268523 A1  Aug. 27, 2020

(30) Foreign Application Priority Data
Sep. 13, 2017 (DE) ..................... 10 2017 008 592.7

(51) Int. Cl.
*A61F 2/44* (2006.01)
*A61F 2/30* (2006.01)

(52) U.S. Cl.
CPC ...... *A61F 2/447* (2013.01); *A61F 2002/3092* (2013.01); *A61F 2002/3093* (2013.01); *A61F 2002/3097* (2013.01); *A61F 2002/30968* (2013.01); *A61F 2002/30978* (2013.01)

(58) Field of Classification Search
CPC .................................. A61F 2/44; A61F 2/447
See application file for complete search history.

(56) References Cited

U.S. PATENT DOCUMENTS

| | | | | |
|---|---|---|---|---|
| 8,623,088 B1 * | 1/2014 | Tohmeh | ................ | A61F 2/4455 623/17.11 |
| 8,900,311 B2 * | 12/2014 | Ciupik | .................. | A61F 2/4465 623/17.16 |
| 2004/0199251 A1 | 10/2004 | McCombe et al. | | |
| 2010/0152853 A1 | 6/2010 | Kirschman | | |

(Continued)

FOREIGN PATENT DOCUMENTS

DE    4318700 C1    11/1994
DE    10113689 C1    8/2002
(Continued)

*Primary Examiner* — Christopher J Beccia
(74) *Attorney, Agent, or Firm* — McGlew and Tuttle, P.C.

(57) ABSTRACT

An intervertebral implant with a support portion (1.1) and a proximal contact portion (1.3) adjoined thereto in the longitudinal direction, is better adapted, as an intervertebral implant, to the contours of the lower and upper sides of the vertebrae that are spaced apart by the implant. An upper side (1.6) and a lower side (1.7) of the implant are configured symmetrically relative to a horizontal center plane (L-Q). In particular a height of the support portion between the transition (U) thereof to the contact portion (1.3) and a distal end face (1.2) facing away from the contact portion (1.3) are greater than the height at the transition (U) and at the distal end face (1.2).

24 Claims, 6 Drawing Sheets

(56) References Cited

U.S. PATENT DOCUMENTS

| | | | | |
|---|---|---|---|---|
| 2010/0286783 A1* | 11/2010 | Lechmann | ................ | A61F 2/44 623/17.12 |
| 2013/0096685 A1* | 4/2013 | Ciupik | .................. | A61F 2/4465 623/17.16 |
| 2014/0031943 A1* | 1/2014 | Yu | ......................... | A61F 2/4611 623/17.16 |
| 2016/0113773 A1* | 4/2016 | Ganem | ................... | A61F 2/447 623/17.16 |

FOREIGN PATENT DOCUMENTS

| | | | |
|---|---|---|---|
| DE | 202013007361 U1 | 3/2014 | |
| DE | 202014003441 U1 | 11/2014 | |
| EP | 2983622 B1 | 12/2016 | |

\* cited by examiner

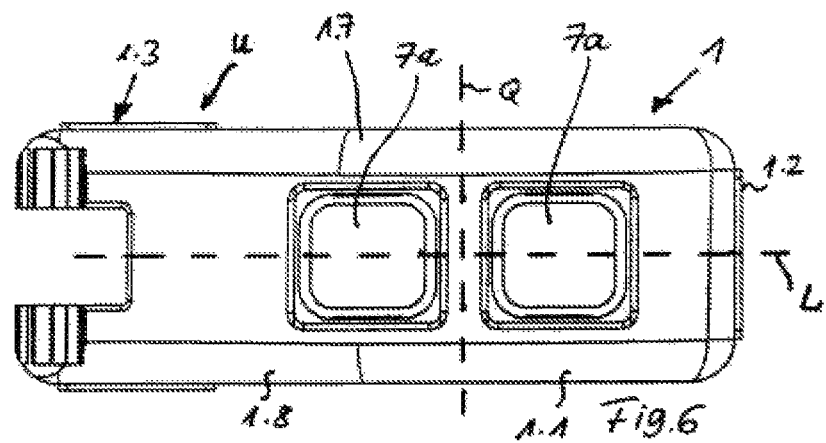
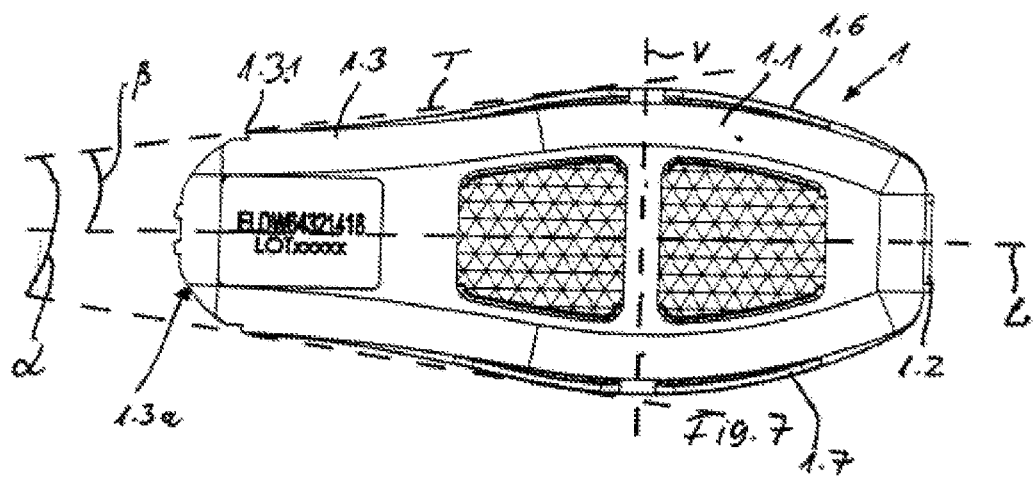

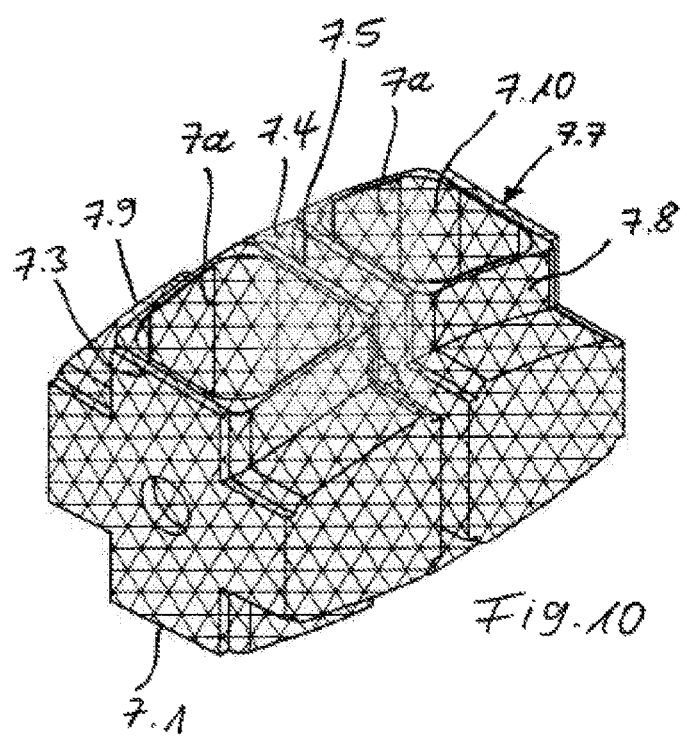

INTERVERTEBRAL IMPLANT

CROSS REFERENCE TO RELATED APPLICATIONS

This application is a United States National Phase Application of International Application, PCT/EP2018/000426, filed Sep. 5, 2018, and claims the benefit of priority under 35 U.S.C. § 119 of German Application 10 2017 008 592.7, filed Sep. 13, 2017, the entire contents of which are incorporated herein by reference.

TECHNICAL FIELD

The invention relates to an intervertebral implant with a support portion and a proximal contact portion adjoining this in the longitudinal direction.

TECHNICAL BACKGROUND

Intervertebral implants are also referred to as interbody cages.

For a number of spinal injuries, especially intervertebral disc damage such as vertebral sliding and instability after a herniated disc, through stenosis and degeneration the spine is stiffened between the two vertebral bodies affected by the damage. For this purpose, implants are inserted between two vertebrae of the spine immediately above one another after removal of a damaged and/or (nerve) damaging intervertebral disc from the intervertebral space or intervertebral disc compartment in order to keep them at the specified distance. The spine is stiffened at least in the area of these two vertebrae. This is referred to as (lumbar) vertebral fusion (Lumbar Interbody Fusion—LIF). If necessary, in minimally invasive spinal surgery, the vertebrae are provided with a rod-screw unit, facet joint screws or translaminar screws and braced against the implant therebetween. In this respect, it is also desirable that the bones grow together with the implant. Such an implant is therefore usually provided with a rough surface.

A generic intervertebral implant is known from DE 20 2014 003 441 U, for example.

SUMMARY

The invention is based on the object of developing a generic intervertebral implant in such a way that it is better adapted to the adjacent vertebrae and of proposing a method for introducing such an implant.

According to the invention, the stated object is achieved in the case of an intervertebral implant in that an upper side and a lower side are formed symmetrically relative to a horizontal center plane.

The implant is configured for insertion by means of minimally invasive operations through the intervertebral foramen as a single implant in the intervertebral space between two vertebrae. It therefore extends in the intervertebral space at finite angles (angle not equal to 0°) relative both to the sagittal and to the frontal plane. Accordingly, the object for solving the problem is also a method for introducing an intervertebral implant, comprising a support portion and a proximal contact portion adjoined thereto by way of a transition area, the upper side and lower side of the intervertebral implant being formed symmetrically relative to a horizontal center plane, characterized in that the implant is inserted minimally-invasively through an intervertebral foramen between two vertebrae as a single implant in the intervertebral space in such a way that the implant comes to lie between the vertebrae at finite angles relative to both a sagittal and to a frontal plane.

Due to the symmetrical design, the desired improved tailoring of the implant to the adjacent vertebral bodies is achieved.

A further development provides that a transition area is formed between the support portion and the contact portion.

For further support, it is provided in a preferred embodiment that the height of the support portion between the transition area to the contact portion and a distal end face facing away from the contact portion is greater than the height at the transition area and at the distal end face, in particular the greatest height is in the middle between the transition area to the contact area and the distal end face facing away therefrom.

A further development provides that the transition area between the support portion and the contact portion is concave. The designs of the implant according to the invention allow the vertebrae between which the implant is disposed to roll optimally on the upper side and lower side of the implant in all directions and therefore, despite there being an inserted implant, allow the spine to move in this area, which is not the case with known implants.

The angle between the tangents to the proximal edge of the implant toward the distal end face and at the central region with the greatest implant height is preferably between 10° and 20°, in particular 12° to 18°, tailored to the corresponding lordosis angle of a patient, that is to say each of these tangents lies at an angle of 5° to 10°, or in a more preferred embodiment between 6° and 9°, relative to the longitudinal center plane of the implant. This supports or restores the natural lordosis of the lumbar spine. The (maximum) height of the implant is preferably adapted to the physical structure of the patient's spine or the corresponding intervertebral region in which the implant is to be attached, and accordingly can have an adjusted height in the range from 8 mm to 18 mm, preferably 10 mm to 16 mm. The same applies to the length of the implant, which should be 25 mm to 35 mm, in particular between 27 mm and 32 mm.

In another extremely preferred embodiment of the invention, it is provided that the height thereof is greater on one longitudinal side than on an opposite longitudinal side. The height of the implant is thus asymmetrical with respect to its vertical center plane. This further supports tailoring to the natural conditions of the upper or lower end face of vertebrae between which the implant is arranged. An implant cannot be inserted centrally between vertebrae and is therefore not aligned therebetween in the direction of the sagittal plane or the sagittal axis from posterior or dorsal to anterior or ventral. Rather, the implant is usually introduced through the intervertebral foramen and is thus at a finite angle in the order of about 45° relative to the sagittal axis/plane. The different heights on the two sides of the implant (with a continuous transition therebetween) result in a better adaptation to the positioning of the implant between the vertebrae. It is particularly provided that the height of the implant is 2 mm less on one side than on the other side. Implants are usually inserted between vertebrae in such a way that they extend dorsal-left to ventral-right—when looking at the patient. In this case, the implant has a left side with a lower height than the right side when viewed from the side proximal end face (more precisely, the starting surface) in the distal direction.

In a further preferred embodiment, an outer frame made of solid supporting parts and an inner core in the form of a lattice body is provided, the lattice body in particular being connected to the frame only at surfaces running parallel in a transverse direction, but is not connected to the frame in surfaces running at a finite angle to these surfaces and edges.

Such an implant is preferably produced by sintering, in particular by means of (selective) electron beam melting ((Selective) Electron Beam Melting, (S)EBM) or by means of laser sintering (LST). Accordingly, the implant is made by sintering such as by means of electron beam melting or laser sintering.

The net-like or lattice-like areas preferably extend from an upper or side surface to the parallel opposite lower or side surface. The result of this is that bone tissue not only grows on the outer surface of the implants, but also grows into the cavities of the lattice-like or mesh-like structure, can penetrate the implant completely and that bone growth is promoted. This creates a firm connection between the implant and the adjacent vertebral body.

By designing the implant with two structural elements, namely an—outer—frame made of compact material and in a compact structure, and an inner lattice body with the net-like or lattice-like structure mentioned, the above-mentioned advantages of complete growth of bone material through the implant and/or the lattice-like structure thereof gives the implant sufficient strength and rigidity.

In addition, the lattice body is connected to the frame only on surfaces running parallel in one direction, namely a transverse direction, but is not connected to the frame in surfaces and edges running at a finite angle to these surfaces. In this way, a decoupling of the outer frame and the lattice body of the implant is achieved in a way that both are decoupled in the longitudinal or main extension direction of the implant (the implant is longer in the insertion direction than in the transverse direction and in the height thereof). If the frame yields to pressure exerted thereon, for example in the area of ribs forming the frame, this is not transferred to the lattice body. The latter remains unaffected and the bone structure that has grown into the lattice body is not impaired or damaged.

In a preferred further development, it is provided that the upper and lower surfaces of the lattice body have the same dimensions as the free spaces which are surrounded by frame components and which surround said surfaces of the lattice body—possibly taking tolerances of up to 0.3 mm into account.

In a further embodiment of the implant according to the invention it is provided that the frame surrounds a cavity in which the lattice body is disposed. A further development provides that the frame has longitudinal ribs running in the longitudinal direction thereof. An extremely preferred embodiment provides that adjacent longitudinal ribs are connected in the middle by transverse ribs. As a result, the stability of the frame and thus of the implant itself is increased even with longer implants. The mesh or lattice structure of the lattice body of the implant can be configured in various ways. In an extremely preferred embodiment, it is provided that the lattice area or lattice body has a diamond structure.

It can also be provided that it has a continuous passage. The passage extends in the longitudinal direction through the frame and in particular also through the lattice body itself. This ensures that the implant can be inserted through a tubular sluice or an endoscope tube—by means of an insertion instrument using a guide wire which extends into the intervertebral space or the intervertebral disc compartment.

A preferred embodiment of the implant according to the invention is characterized in that the lattice-like regions or the lattice body have a lattice opening diameter of each opening of 0.5 mm to 3.5 mm, preferably on the outside of the implant an opening diameter of each opening in an order of magnitude of 0.5 mm to 0.7 mm.

As mentioned, an implant can be produced in particular by (selective) electron beam melting (S)EBM) or laser sintering technology (LST) from titanium alloy, in particular Ti6Al4V according to ISO 5832-3. The component—implant—is produced by melting metal powder using an electron beam or laser beam in a high vacuum. This enables undercuts to be created without lost molds or cores. Using an electron beam or laser beam as the energy source, the metal powder is melted in a targeted manner, whereby compact components of almost any geometry can be produced directly from design data. A layer of powder is alternately applied to the previous layer by means of a doctor blade and exposed to the electron beam. In this way, the desired component is generated in layers.

A further embodiment of the method according to the invention provides that the implant is introduced into the intervertebral space in such a way that it lies at an angle between 40° and 50°, preferably 45°, relative to the sagittal plane. In a preferred embodiment it is provided that the method uses an implant according to the invention which has one or more of the configurations of the implant described above.

Further advantages and features of the invention result from the claims and from the following description, in which an embodiment of the implant according to the invention is explained in detail with reference to the drawing. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in the preferred embodiment of the invention is illustrated.

BRIEF DESCRIPTION OF THE DRAWINGS

In the drawings:

FIG. 6 is a top view of the implant from above;

FIG. 7 is a side view of the implant;

FIG. 10 is a perspective view of the lattice rim of the implant.

DESCRIPTION OF PREFERRED EMBODIMENTS

Figure 1:
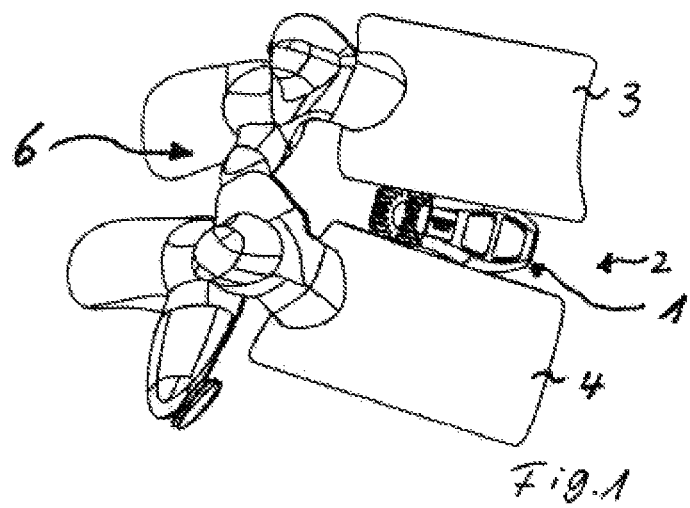
FIG. 1 is a view of the horizontal axis X showing the arrangement of an implant according to the invention between two vertebrae.
Figure 2:
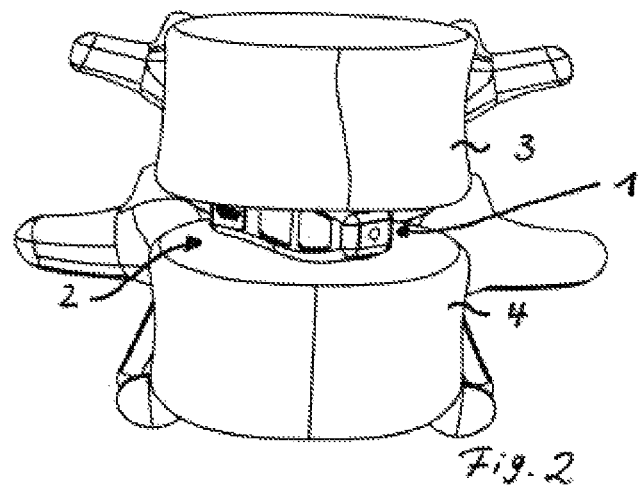
FIG. 2 is a dorsal view along the sagittal axis showing the arrangement of an implant according to the invention between two vertebrae.

Referring to the drawings, if, due to damage to an intervertebral disc of a patient's spine, the intervertebral disc is to be removed from the intervertebral space 2 between two superimposed vertebrae 3, 4, an intervertebral implant 1 is used instead to hold the vertebrae 3, 4 at a suitable distance and in an inclined orientation to one another, as shown in FIGS. 1 and 2. The implant 1 is configured such that the implant 1 can grow together with the vertebrae 3, 4.

Figure 3:
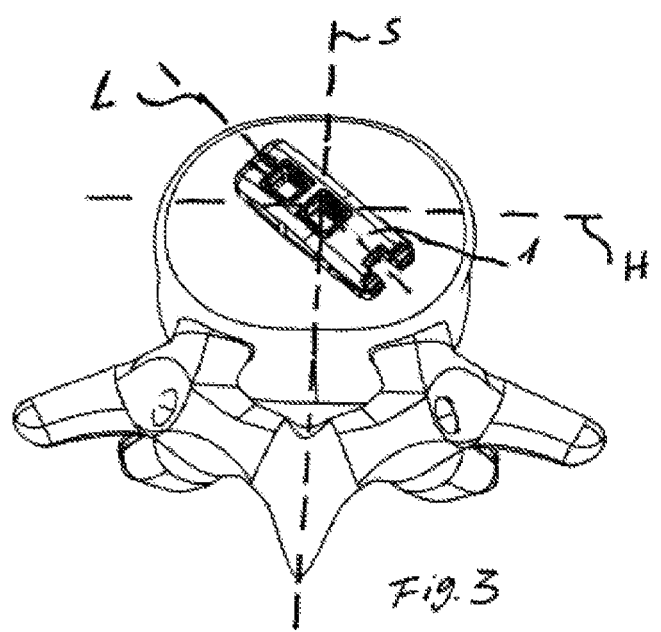
FIG. 3 is a top perspective view of an implant resting on a lower vertebra.
Figure 4:
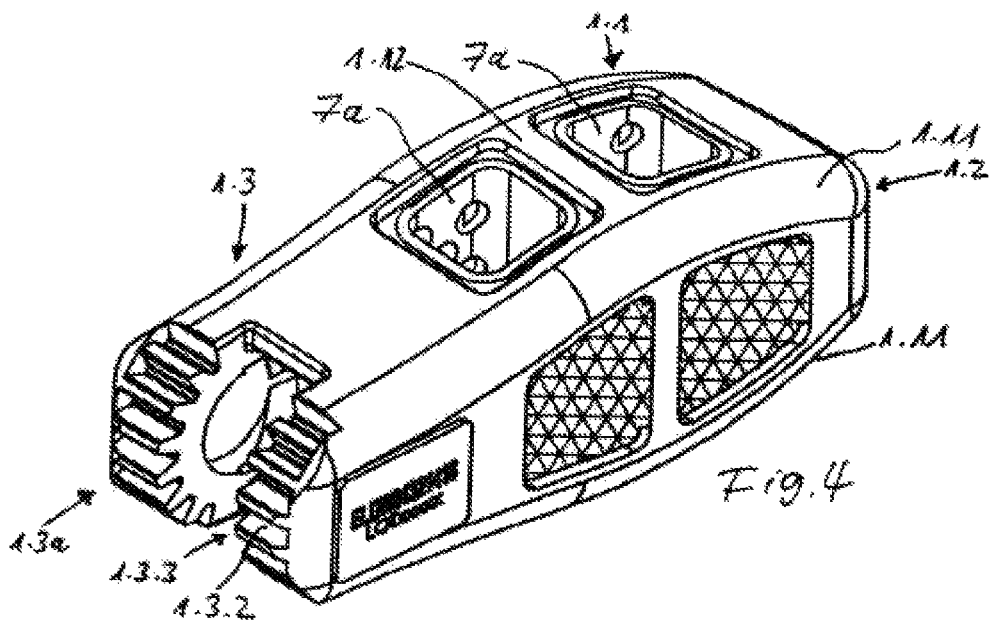
FIG. 4 is a perspective view of the outer contour of an implant from the proximal end.
Figure 5:
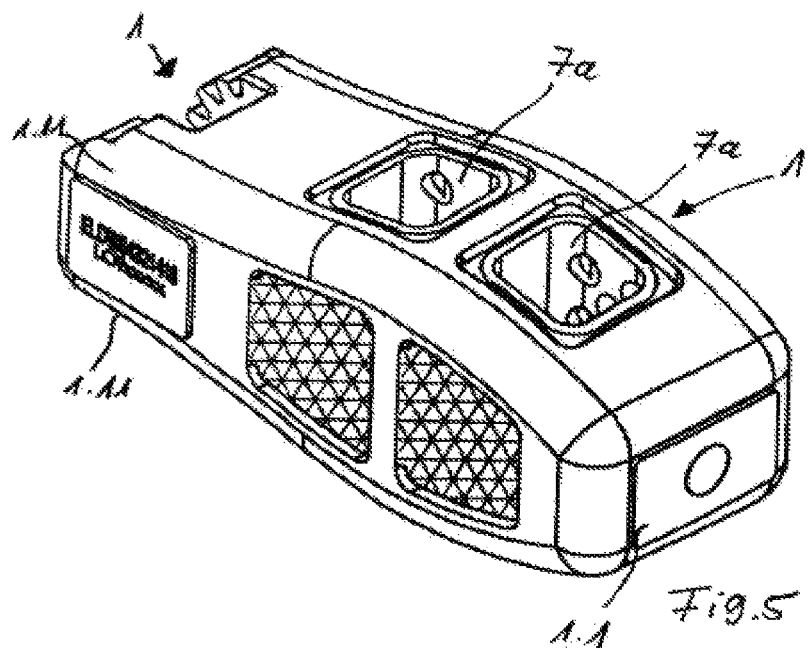
FIG. 5 is a perspective view of the outer contour of the implant from the distal end.

The implant 1 according to the invention is inserted in a minimally invasive manner through an—enlarged—access through the—here: right—intervertebral foramen 6 between the two vertebrae 3, 4 and as such lies between the horizontal and sagittal axes H, S of the patient's body as seen in FIG. 3 as a single implant whose longitudinal central axis L is at an angle of approximately 45° relative to the sagittal axis S of the patient's body or spine, i.e. whose longitudinal central axis L lies approximately along the bisector therebetween. While the implant 1 according to the present embodiment was inserted through the left intervertebral foramen between the two vertebrae 3, 4—when looking at the front of the patient—in principle it can also be introduced along the right intervertebral foramen 6.

The implant is described below for the purposes of the access and arrangement shown; upon access through the right intervertebral foramen 6, the implant is configured as a mirror image relative to the vertical of the longitudinal center plane L-V (spanned by the horizontal longitudinal and transverse axes L, Q; described in more detail below) of the implant shown and described below.

Figure 8:
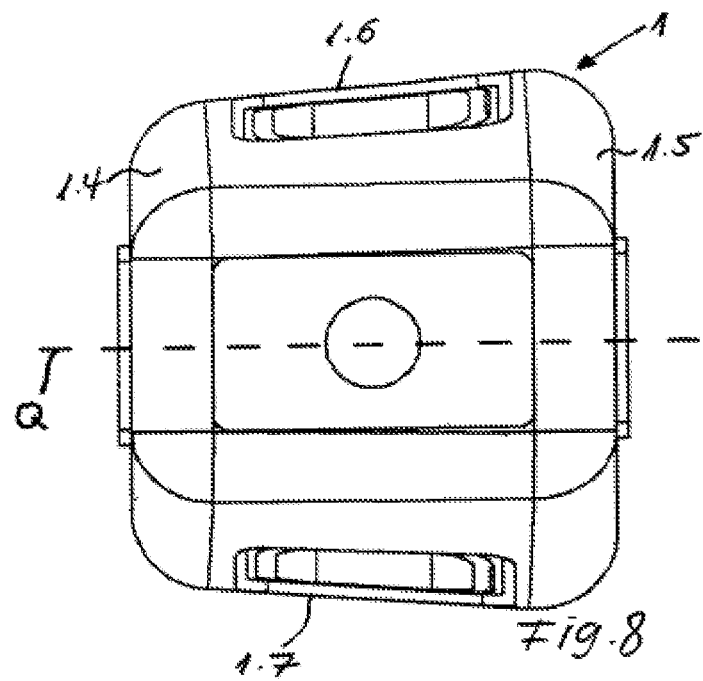
FIG. 8 is a view of the distal end face of the implant.

In FIGS. 6-8, the longitudinal central axis L, horizontal transverse axis Q and vertical axis V of the implant 1 are shown and defined by the illustrations. The implant 1 has a longitudinal extension along the longitudinal central axis L thereof, the extension being substantially greater than the extension in the direction of the vertical axis V and the transverse axis Q—a dimension of at least 1.5 times as much. A horizontal center plane L-Q is determined by the longitudinal axis L and the transverse axis Q, a vertical plane L-V is determined by the longitudinal axis L and the vertical axis V and a transverse plane Q-V is determined by the transverse axis Q and the vertical axis V.

The implant has a support portion 1.1 with a distal end face 1.2. This is adjoined proximally by a transition area U—corresponding to the line U—to a proximal contact portion 1.3, at which a tool for inserting the implant 1 into the intervertebral space can engage, as is described in particular in DE 20 2013 007 361 U. With such an angular orientation, the implant 1 is introduced into the intervertebral space between the vertebrae 3, 4 in the manner described in this document through the—expanded—intervertebral foramen.

The implant 1 according to the invention is configured with the upper side 1.6 and lower side 1.7 thereof being symmetrical relative to the horizontal center plane L-Q. The support portion 1.1 of the implant has its greatest height in the area of the vertical central axis V or the vertical plane V-Q, whereas on the one hand the height of the free distal end face 1.1 and on the other hand the height in the transition area U to the contact portion 1.3 is lower than the height in the vertical center plane V-Q. The implant 1 therefore has the shape of a double wedge in the longitudinal direction.

Tangents T from a proximal edge 1.3.1 of the contact portion 1.3 to the proximal height in the central region of the support portion 1.1 have an angle relative to one another of between 10° and 20°, preferably 12° to 18°, and corresponding to the longitudinal central axis or plane L-Q, the tangents have an angle of from 5° to 10° or 6° to 9°. To accommodate the lordosis angle between the patient's vertebrae between which the implant 1 is inserted, an implant with a very specific angle α or β is selected which is suitable for the patient.

Figure 9:
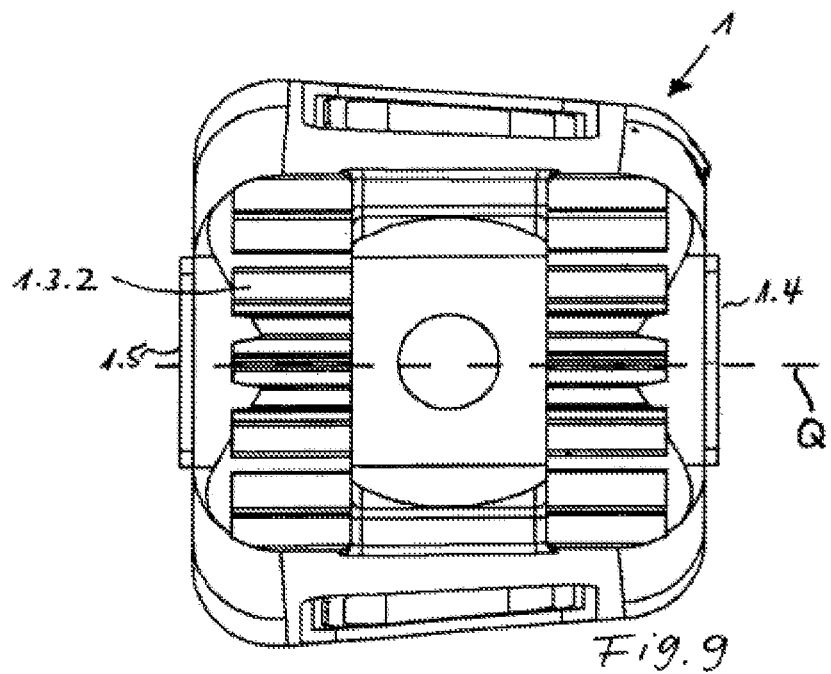
FIG. 9 is a view from an end face to the contact portion of the implant.

As can be seen in particular from FIGS. 8 and 9, the implant 1 is configured asymmetrically relative to the longitudinal vertical plane L-V. It has a greater height in the area of the left vertical longitudinal side 1.5 than on the right longitudinal side 1.4—as seen from the view to the proximal end face 1.3a (FIG. 9).

The height difference of the two longitudinal sides 1.4, 1.5 in the middle of the support portion 1.1 is approximately 1.5 mm to 3 mm here, preferably 2 mm. Due to this height difference, i.e. inclinations of the upper side 1.6 and lower side 1.7, the implant is better adapted to the anatomical relationships of the bottom of the upper vertebra 3 and the top of the bottom vertebra 4 than would be the case with a parallel alignment of the upper and lower sides 1.6, 1.7. For the sake of good order, it should be pointed out once again that the height difference, i.e. inclination of the upper side 1.6 and lower side 1.7, described above relates to an implant to be inserted through the left intervertebral foramen in the defined manner, whereas an implant to be inserted through the right intervertebral foramen is configured in like manner to be mirror-symmetrical relative to the longitudinal vertical plane L-V.

Apart from the two portions described, the support portion 1.1 and the contact portion 1.3, the implant according to the invention comprises the components of an outer rigid frame 1.8 and a lattice-like inner core 1.9 in the form of a lattice body 7, the latter being shown in FIG. 10. Components 1.8 and 1.9 form the implant 1 in one piece. Because of the openings in the upper walls and longitudinal side walls visible in the outer frame 1.8, bone can grow into the lattice-like inner core 1.9, grow together with the core and thus result in a stable connection.

The lattice body 7 has a lattice structure, preferably a diamond lattice structure with thin ribs 7.1 and free spaces therebetween, the dimensions of the ribs 7.1, in particular their thickness (in a direction perpendicular to the direction of extension of the ribs 7.1 between two node points at which the each of the ribs is connected with further ribs of the lattice), being small compared to all structural component dimensions of the frame 1.8, such as a width of struts of the frame 1.8. The proportions are at least 1:3. The same applies to the length of struts 7.1 of the lattice body 7 between two node points and to the longitudinal dimensions of structural parts of the frame 1.8, such as the above-mentioned ribs, so that the ratio here is at least 1:3.

The frame 1.8 has four longitudinal struts 1.11 which connect the distal end face 1.2 of the implant 1 and the proximal contact portion region 1.3 and enclose a cavity therewith in which the lattice body 7 is located when the implant is complete. The lattice body has two vertical openings 7a. Each longitudinal strut 1.11 is connected to the other at the end face and in the middle, that is to say at approximately half the length of the support portion 1.1, by way of transverse ribs 1.12. Accordingly, a passage remains between the transverse ribs 1.12. Corresponding passages can also be found in particular on the distal end face 1.2.

In an extremely preferred embodiment, the lattice body 7 and the frame 1.8 are connected to one another—in one piece—only in (surface) areas which are perpendicular to the longitudinal direction L and thus are transverse areas, as is described in more detail in DE 20 2013 007 361 U.

In contrast, longitudinal surfaces, such as 7.8 and also longitudinal edges, such as 7.9, of the lattice body 7 are not firmly connected to the frame 1.8. In addition, the dimensions of the upper surfaces 7.10 and the lower surfaces parallel thereto on the bottom of the lattice body 7 correspond to the recesses, i.e. the regions left open by the longitudinal struts 1.11, the transverse ribs 1.12 and the end region 1.2. This means that when pressure is exerted on the longitudinal ribs of the frame 1.8 by the vertebral bodies 3, 4, the pressure is not transmitted to the lattice body 7 on the longitudinal sides, the lattice body thus remaining undeformed and its task of bone material growing into these honeycomb or intermediate spaces of the lattice body 7 is ensured even under these circumstances. The continuous longitudinal passage of the implant 1 enables the implant to be inserted into the intervertebral compartment via a guide wire.

The proximal contact portion 1.3 has serrations 1.3.2 on the proximally directed end face thereof. These serve to fix a predetermined angular orientation between the insertion instrument and the implant 1 when the implant 1 is fixed to the distal end of an insertion instrument (DE 20 2013 007 361 U and EP 2 983 622 B1) by way of axial tensioning between a hammer-like locking member of the insertion instrument and an abutment thereof. The serrations 1.3.2 are formed by successive teeth along a circular arc. There is a serration 1.3.2 on each side of a proximal inlet 1.3.3 or of the opening of the implant 1 on the proximal end face of the contact portion 1.3.

The design (e.g. number, distance, shape) of the serrations 1.3.1 can be matched to the insertion instrument. This enables optimum compatibility with the insertion instrument, increased stability of the connection between abutments of the insertion instrument and proximal contact portion 1.3 of the implant 1, and, on the other hand, a plurality of connection angles.

An implant 1 according to the invention is introduced by means of an insertion instrument, as is shown and described in DE 20 2013 007 361 U and EP 2 983 622 B1. A locking element has a hammer-like locking part which can be rotated about its longitudinal axis and which is inserted in a vertical orientation into the passage 1.3.2 of the proximal contact portion 1.3 of the implant 1. For this purpose, the implant 1 has an undercut opening 1.3.3 on its proximal end face, the opening cross section of said opening corresponding to the locking element of the insertion instrument; the undercut opening forms a locking element on the implant 1, which enables the insertion instrument and the implant 1 to be locked.

The hammer-like locking part of the insertion instrument is subsequently pivoted by 90° relative to an external tube provided, so that the locking part engages in undercuts on the inside of the wall of the proximal contact portion 1.3. By means of tensioning devices at the proximal end of the insertion instrument, the hammer-like locking part and concavely-curved end edges are braced against one another at an abutment provided distally on the outer tube, serrations being engaged to the locking part at the proximal contact portion 1.3 of the implant 1. As a result, the implant 1 is held firmly on the insertion instrument. This enables the implant 1 to be moved in the direction of extension thereof and with a component to the direction of extension of the insertion instrument. Insofar as the proximal contact portion 1.3 of the implant 1 has a serration on the (outer) proximal end face thereof, this also assures an assumed angular position between the insertion instrument and the implant 1. Nevertheless, a different angle of alignment is possible between the insertion instrument and the implant in the direction perpendicular to the longitudinal extent L of both at considerable angles of up to 30° and more.

While specific embodiments of the invention have been shown and described in detail to illustrate the application of the principles of the invention, it will be understood that the invention may be embodied otherwise without departing from such principles.

The invention claimed is:

1. An intervertebral implant comprising:
   a support portion; and
   a proximal contact portion adjoined to the support portion in a longitudinal direction, wherein the support portion with adjoined proximal contact portion has an upper side and a lower side that are symmetrical relative to a horizontal center plane, wherein a concave transition area is formed between the support portion and the contact portion, wherein a height of the support portion between the transition area to the contact portion and a distal end face remote from the contact portion is greater than the height at the transition area and at the distal end face and the greatest height is formed in the middle between the transition area to the contact portion and the distal end face remote therefrom.

2. The implant according to claim 1, wherein a height of the implant is greater on one longitudinal side than on an opposite longitudinal side.

3. The implant according to claim 1, wherein the implant comprises:
   an outer frame made of solid supporting parts; and
   an inner core in the form of a lattice body.

4. The implant according to claim 3, wherein the lattice body is connected to the frame only at transverse surfaces running parallel in a transverse direction, but is not connected to the frame at surfaces and edges which run at a finite angle relative to said transverse surfaces.

5. The implant according to claim 3, wherein the frame, which determines an outer contour, and the core located therewithin are formed in one piece.

6. The implant according to claim 1, wherein the implant is produced by sintering, such as by means of laser sintering.

7. The implant according to claim 3, wherein the implant is produced by means of electron beam melting.

8. The implant according to claim 3, wherein:
   upper and lower surfaces of the core have same dimensions as open spaces surrounded by frame components; and
   said open spaces comprise surfaces of the lattice body.

9. The implant according to claim 3, wherein the frame surrounds a cavity in which the lattice body of the core is disposed.

10. The implant according to claim 3, wherein the frame has adjacent longitudinal ribs being connected centrally by transverse ribs.

11. The implant according to claim 3, wherein the lattice body has a diamond structure.

12. The implant according to claim 3, wherein the implant has a continuous passage along a longitudinal central axis.

13. The implant according to claim 3, wherein the lattice body has openings with lattice opening diameters of each opening of 0.5 mm to 3.5 mm.

14. The implant according to claim 13, wherein the lattice body has an outside with openings and opening diameters of each opening are in the order of magnitude of 0.5 mm to 0.7 mm.

15. The implant according to claim 1, wherein the proximal contact area is for connecting the implant to an insertion instrument and has undercut recesses on an inside of side walls of the implant, the recesses enabling an angularly movable undercut connection.

16. The implant according to claim 1, wherein the contact area has a cutout on the upper side which enables angular mobility of the implant.

17. The implant according to claim 1, wherein a proximal end face of the contact area has serrations and circular sections, the serrations being formed in succession in a vertical direction on the circular sections and the serrations being disposed on both sides of a proximal passage formed centrally on the proximal end face.

18. A method for introducing an intervertebral implant, the method comprising the steps of:
provide the implant with a support portion and with a proximal contact area adjoined thereto by way of a transition area, the upper side and the lower side of the intervertebral implant being symmetrical relative to a horizontal center plane, wherein a concave transition area is formed between the support portion and the contact portion, wherein a height of the support portion between the transition area to the contact portion and a distal end face remote from the contact portion is greater than the height at the transition area and at the distal end face and the greatest height is formed in the middle between the transition area to the contact portion and the distal end face remote therefrom;
inserting the implant minimally-invasively through an intervertebral foramen between two vertebrae as a single implant in an intervertebral space such that the implant comes to lie between the vertebrae at finite angles of both a sagittal and a frontal plane.

19. The method according to claim 18, wherein the implant is introduced into the intervertebral space such that the implant lies in the intervertebral space at an angle of between 40° and 50°, relative to the sagittal plane.

20. The method according to claim 18, wherein the intervertebral implant introduced into the intervertebral space between two vertebrae comprises an outer frame made of solid supporting parts and an inner core lattice body.

21. An intervertebral implant comprising:
a support portion comprising a distal end surface and a longitudinal axis; and
a proximal contact portion connected to the support portion in a longitudinal direction with respect to the longitudinal axis, the proximal contact portion being located opposite the distal end surface, wherein the support portion with the proximal contact portion connected thereto has an upper side and a lower side that are symmetrical relative to a horizontal center plane, wherein a concave transition area is formed between the support portion and the contact portion, wherein a height of the support portion between the transition area and the distal end surface is greater than a height at the transition area and a height at the distal end surface and a greatest height is formed in a middle of the support portion between the transition area and the distal end surface, the middle area being located at a spaced location from the concave transition area.

22. The implant according to claim 21, wherein a height of the implant is greater on one longitudinal side than on an opposite longitudinal side.

23. The implant according to claim 21, wherein the implant comprises:
an outer frame made of solid supporting parts; and
an inner core in the form of a lattice body.

24. The implant according to claim 23, wherein the lattice body is connected to the frame only at transverse surfaces running parallel in a transverse direction, but is not connected to the frame at surfaces and edges which run at a finite angle relative to said transverse surfaces.

* * * * *